(12) United States Patent
Muyari

(10) Patent No.: US 8,801,708 B2
(45) Date of Patent: Aug. 12, 2014

(54) ENDOSCOPIC-USE TREATMENT INSTRUMENT

(75) Inventor: Yuta Muyari, Tokyo (JP)

(73) Assignee: Olympus Medical Systems Corp. (JP)

( * ) Notice: Subject to any disclaimer, the term of this patent is extended or adjusted under 35 U.S.C. 154(b) by 1445 days.

(21) Appl. No.: 12/208,400

(22) Filed: Sep. 11, 2008

(65) Prior Publication Data

US 2009/0076319 A1 Mar. 19, 2009

(30) Foreign Application Priority Data

Sep. 18, 2007 (JP) .............................. P2007-241366

(51) Int. Cl.
*A61B 18/18* (2006.01)
(52) U.S. Cl.
USPC ................................ 606/47; 606/46; 606/113
(58) Field of Classification Search
USPC ............................................. 606/46–47, 113
See application file for complete search history.

(56) References Cited

U.S. PATENT DOCUMENTS

| 5,049,124 A | 9/1991 | Bales, Jr. .......................... 604/22 |
| 2003/0125731 A1* | 7/2003 | Smith et al. ...................... 606/47 |
| 2004/0172018 A1* | 9/2004 | Okada .............................. 606/46 |

FOREIGN PATENT DOCUMENTS

| EP | 1849419 | 10/2007 |
| GB | 2321193 | 7/1998 |
| JP | S57-145654 | 9/1982 |
| JP | 10-146345 | 6/1998 |
| JP | 2004-261372 | 9/2004 |
| JP | 2007-215787 | 8/2007 |

OTHER PUBLICATIONS

Extended Search Report mailed Jan. 29, 2009 in corresponding European Application No. 08016216.7-2310.
Office Action issued by the Japanese Patent Office on Jun. 5, 2012 in connection with corresponding Japanese Patent Application No. 2007-241366.
Translation of Office Action issued by the Japanese Patent Office on Jun. 5, 2012 in connection with corresponding Japanese Patent Application No. 2007-241366.

* cited by examiner

*Primary Examiner* — Jaymi Della
(74) *Attorney, Agent, or Firm* — Ostrolenk Faber LLP

(57) ABSTRACT

An endoscopic-use treatment instrument includes: a wire; an Y-shaped knife formed by a flexible material and is disposed at the distal end of the wire and used for treatment conducted in a body cavity; a flexible sheath having the wire passing therethrough; an operation section provided to the proximal end of the wire and capable of rotating the wire around an axial line; a cylindrical bearing fixed to the distal end of the sheath; a rotative member inserted into the bearing and capable of freely rotating relative to the bearing; and a regulator section provided to the rotative member and regulating the rotation of the treatment member relative to the rotative member around the axial line. The rotation of the Y-shape knife relative to the rotative member around the axial line is regulated when the Y-shape knife makes contact with the regulator section.

4 Claims, 6 Drawing Sheets

ENDOSCOPIC-USE TREATMENT INSTRUMENT

This application claims priority to Japanese Patent Application No. 2007-241366, filed on Sep. 18, 2007.

BACKGROUND OF THE INVENTION

1. Field of the Invention

The present invention relates to an endoscopic-use treatment instrument inserted into an operation channel of an endoscope apparatus.

2. Background Art

Endoscopic Submucosal Dissection (ESD) is a commonly known living-mucosal-tissue resection method using an endoscope including: fully incising a normal mucosa developed outside relative to an affected site developed on the surface of gastrointestinal tract, removing a submucosa; and resecting the affected site.

In a manipulation associated with the aforementioned method, an endoscopic-use treatment instrument uses various treatment mechanisms provided to the distal end of a wire inserted into an operation channel of an endoscope and projected from the distal end of the endoscope (for example, see Patent Document 1). In some cases, the treatment instrument needs to rotate a distal end mechanism to obtain more desirable correlation between an treatment object tissue and the distal end mechanism.

Patent Document 1: Japanese Unexamined Patent Application, First Publication No. S57-145654

In case of rotating the distal end mechanism, a user rotates a proximal operation section having the proximal end of a wire fixed thereto to apply rotational torque to the distal end mechanism. However, the distal end mechanism hardly rotates if the distal end mechanism has a shape expanding outward in a radial direction in the exterior of the sheath 111 having a wire 110 passing therethrough as shown in FIG. 9 and makes friction force upon making contact with the inner surface of a sheath 111 and with an insulative member 113 fixed in the sheath 111.

The distal end mechanism in this case makes not a gradual rotation based on applied torque but so called intermittent rotation in which rotation occurs when the applied torque exceeds a predetermined value. The occurrence of intermittent rotation is problematic because it is difficult to position the distal end mechanism relative to an object tissue based on irregular correlation between rotational manipulation and the rotation amount of the distal end mechanism.

SUMMARY OF THE INVENTION

The present invention was conceived in consideration of the aforementioned circumstances, and an object thereof is to provide an endoscopic-use treatment instrument in which rotational operation amount corresponds to rotational amount of a distal end mechanism desirably.

An endoscopic-use treatment instrument according to the present invention includes: a wire; an treatment member formed by a flexible material and is disposed at the distal end of the wire and used for treatment conducted in a body cavity; a flexible sheath having the wire passing therethrough; an operation section provided to the proximal end of the wire and capable of rotating the wire around an axial line; a cylindrical bearing fixed to the distal end of the sheath; a rotative member inserted into the bearing and capable of freely rotating relative to the bearing; and a regulator section provided to the rotative member and regulating the rotation of the treatment member relative to the rotative member around the axial line, so that the treatment member is urged to expand outward in a radial direction of the sheath when the treatment member is in the exterior of the sheath, and the rotation of the treatment member relative to the rotative member around the axial line is regulated when the treatment member makes contact with the regulator section.

According to the endoscopic-use treatment instrument of the present invention, the treatment instrument formed unitarily with the rotative member rotates desirably relative to the sheath and the bearing since the treatment instrument makes contact with the regulator section, and the rotation of the treatment instrument around the axial line relative to the rotative member is regulated.

The regulator section may be formed at, at least, an inner periphery surface of the rotative member, a distal end surface of the rotative member, and a proximal end surface of the rotative member.

The regulator section may be provided at a plurality of points in the circumference direction of the rotative member. In this case, idle rotation amount can be reduced until the treatment instrument makes contact with the regulator section.

The endoscopic-use treatment instrument according to the present invention may further include a current-carrying member, disposed to make contact with the wire, for supplying electric current to the wire, wherein the treatment member is a wire treatment electrode, and the regulator section is formed by insulative material.

According to the endoscopic-use treatment instrument of the present invention, desirable treatment can be conducted since the treatment instrument to which electric current is supplied can be insulated by the regulator member desirably.

According to the endoscopic-use treatment instrument of the present invention, the endoscopic-use treatment instrument can be configured in which rotational operation amount of the operation section corresponds to rotational amount of the treatment member provided to the distal end desirably.

DETAILED DESCRIPTION OF THE INVENTION

An endoscopic-use treatment instrument (simply hereinafter called a treatment instrument) according to an embodiment of the present invention will be explained with reference to FIGS. 1 to 8.

Figure 1:
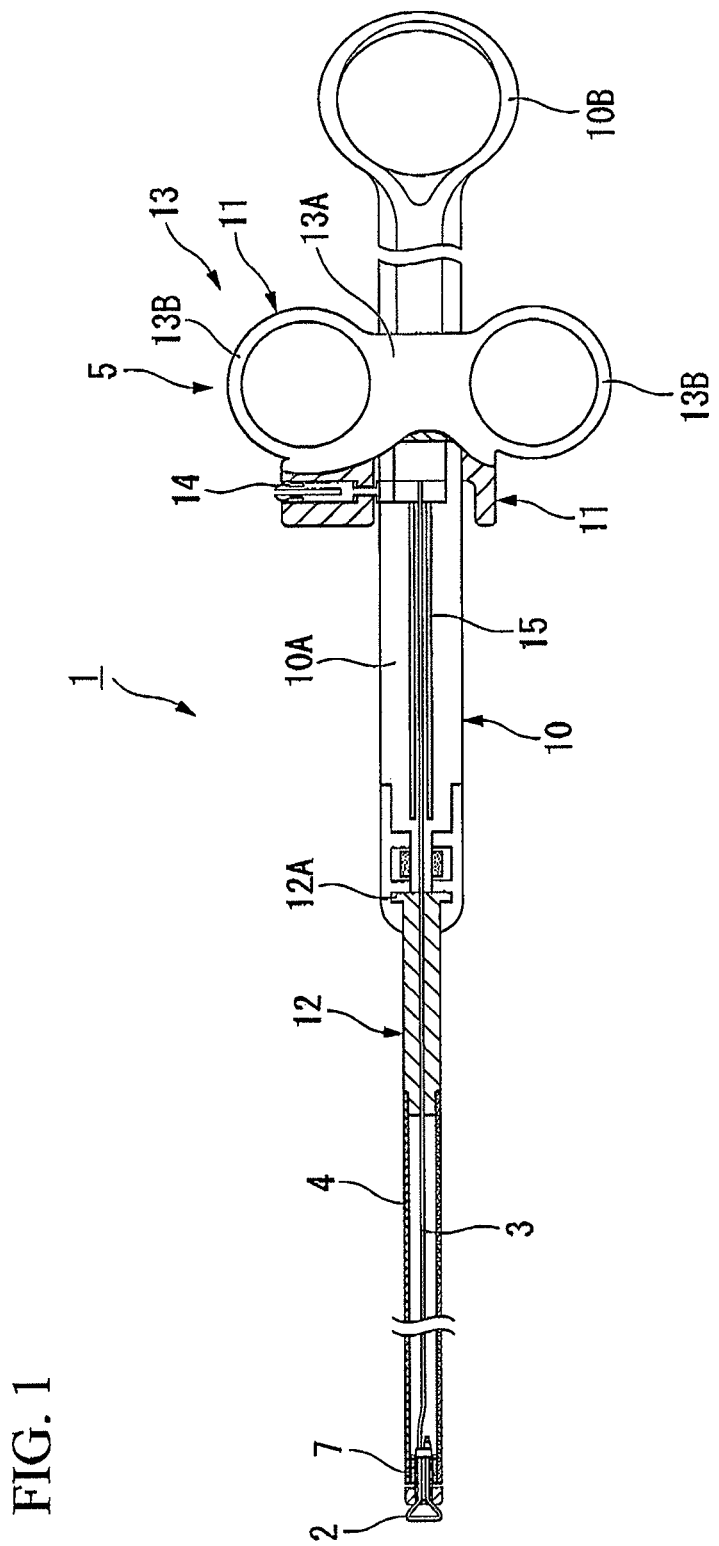
FIG. 1 shows a endoscopic-use treatment instrument according to an embodiment of the present invention in fragmentary sectional view.

FIG. 1 shows a treatment instrument 1 of the present embodiment in a partial cross-sectional view. The treatment instrument 1 includes a wire 3 having a Y-shaped knife (treatment member, instrument electrode) 2 attached to the distal end thereof; a sheath 4 having the wire 3 passing therethrough; and an operation section 5 for operating the wire 3 and the sheath 4.

The Y-shaped knife (hereinafter simply called knife) 2 is formed by bending a flexible wire made from stainless-steel, etc. and spreading it into a substantial Y-shape outward in a radial direction of the sheath in the exterior of the sheath 4. The knife 2 connected to a high-frequency power supply is used for treatment, e.g. ESD as explained later.

Figure 2:
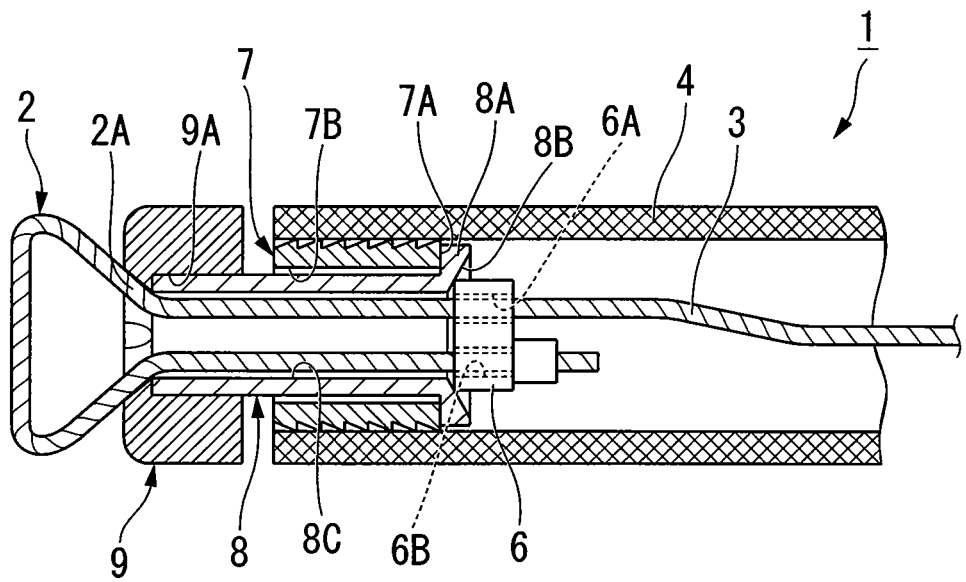
FIG. 2 shows the vicinity of distal end of the endoscopic-use treatment instrument in fragmentary enlarged sectional view.

FIG. 2 is an enlarged view of the vicinity of the distal end of the treatment instrument 1. The wire 3 made of metal having superior torque transmissibility, e.g., stainless steel is inserted through the sheath 4 that will be explained later. As shown in FIG. 2, the wire 3 is inserted through a hole 6A formed in a substantially disk-shaped stopper 6. Upon being bent in a Y-shape, the end section of the inserted wire 3 serving for the knife 2 is entered the sheath 4 and inserted and fixed in a hole 6B formed in the stopper 6. That is, the knife 2 and the wire 3 are formed continuously with a common material.

The sheath 4 is an insulative and flexible tubular member made of resin etc. A substantially cylindrical bearing 7 is fixed to the front end of the sheath 4 by crimping method or bonding method, etc. A substantially cylindrical rotational member 8 made from metal, etc. is inserted into the bearing 7 so that the rotational member 8 is freely rotative around the axial line of the bearing 7.

The rotational member 8 has a flange 8A at the rear end thereof so that the rotational member 8 upon abutting to the rear end 7A of the bearing 7 may not move ahead from there. The knife 2 passing through the rotational member 8 is capable of extending and retracting relative to the distal end of the sheath 4. In addition, the stopper 6 is configured to not move proximally upon abutting to a taper surface 8B formed at the proximal end of the rotational member 8.

In addition, an inner periphery 7B of the bearing 7 and an outer periphery 8C of the rotational member 8 are formed smoothly so to reduce a friction force between two components.

A substantial disk-shaped regulator member 9 for regulating the rotation of the knife 2 around the axial line of the rotational member 8 is fixed to the distal end of the rotational member 8 unitarily with the rotational member 8. The regulator member 9 made of an insulative material e.g., ceramic may not have to be insulative in a case where electricity is not applied to a mechanism provided to the distal end of the wire 3.

A through-hole 9A is formed in the regulator member 9 along the axial line, and the regulator member 9 is attached to the rotational member 8 in the exterior of the sheath 4.

Figure 3A:
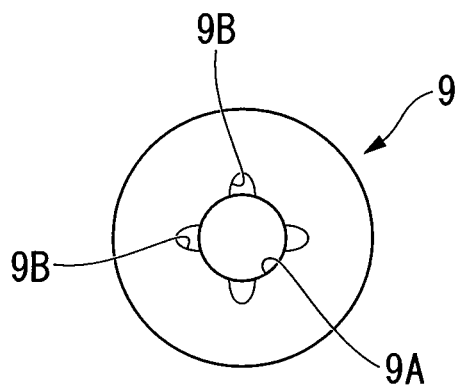
FIGS. 3A and 3B show a regulator member of the endoscopic-use treatment instrument viewed from the distal end thereof.
Figure 3B:
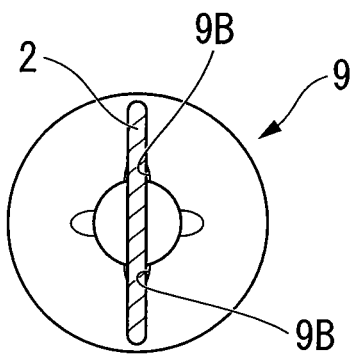

FIGS. 3A and 3B show the regulator member 9 viewed from the distal end thereof. As shown in FIG. 3A, grooves (regulator sections) 9B each having a predetermined depth are provided at four points and formed outward in horizontal and vertical radial directions of the distal end of a through-hole 9A. The width of the groove 9B is set to be substantially the same as the diameter of the knife 2 so that an expansion section 2A can engage with the grooves 9B upon protruding the knife 2 from the regulator member 9 and expanding in the radial directions. Although a pair of grooves 9B are operable when they are provided at two points opposing on the through-hole 9A work, the disposition thereof is not limited to two pairs or four points as shown in FIG. 3A. For example, a pair of them may be disposed in two points, and three or more pairs of them may be disposed in six or more points.

FIG. 1 shows the configuration of the operation section 5 provided with a main body 10 having the sheath 4 fixed thereto; and a slider 11 having the wire 3 fixed thereto.

The bar-shaped main body 10 has a guide groove 10A extending in an axial direction thereof that slides the slider 11. Fixed to the distal end of the main body 10 is a tubular rotor 12 which is capable of freely rotating around the axial line relative to the main body 10 and has a disk-shaped engagement section 12A. The proximal end of the sheath 4 is fixed to the distal end of the rotor 12. That is, the sheath 4 fixed to the rotor 12 is freely rotative in a circumference direction relative to the main body 10. Provided to the proximal end of the main body 10 is a finger hook ring 10B for operation.

The slider 11 includes a operation member 13 which has a cylindrical section 13A surrounding the outer periphery of the main body 10 and a finger hook handle 13B for operation; and a plug (current-carrying member) 14 attached to the operation member 13 and connected to a high-frequency power supply, not shown in the drawing. The proximal end of the wire 3 inserted through the rotor 12 is inserted through a buckling-prevention pipe 15 made of rigid material. The proximal end of the wire 3 and the proximal end of the buckling-prevention pipe 15 are connected and fixed to the plug 14 in the guide groove 10A by fixing means, e.g., screws not shown in the drawing. That is, the slider 11 and the wire 3 are attached to the main body 10 and are capable of freely sliding in an axial direction along the guide groove 10A.

Operation using the treatment instrument 1 having the aforementioned configuration will be explained as follows with reference to a case of conducting ESD using the treatment instrument 1.

In the beginning, the insertion section of an endoscope is inserted into body cavity of a patient, etc., and the distal end of the insertion section is moved to the vicinity of treatment object tissue.

Figure 5:
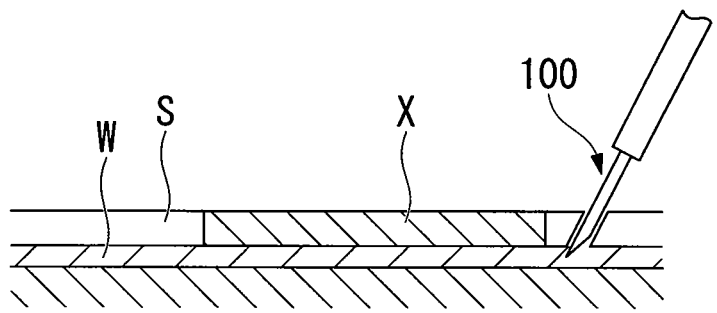
FIG. 5 illustrates a step of ESD.
Figure 6:
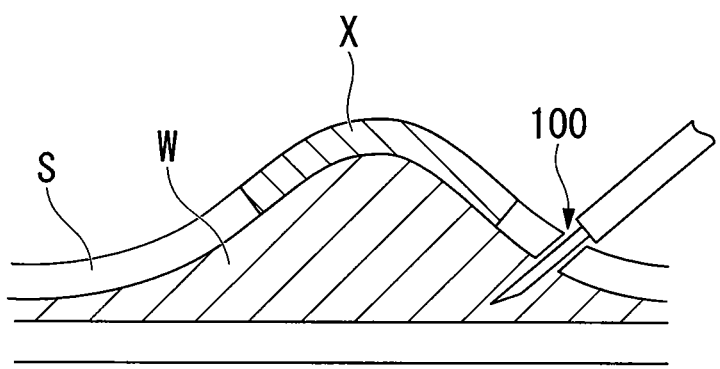
FIG. 6 illustrates a step of ESD.

Subsequently, as shown in FIG. 5, an injection needle 100 is introduced into the body cavity through an operation channel of an endoscope which is not shown in the drawing; normal saline solution is injected into submucosa W in the vicinity of an affected site X which is about to be dissected; and the affected site X is bulged as shown in FIG. 6. It should be noted that it is desirable to disperse colorant around the affected site X so as to distinguish the border of the affected site X prior to the injection; and to make marking to mucosa S at a plurality of positions surrounding the affected site X by using a commonly known round-bar-shaped high-frequency knife 101.

Figure 7:
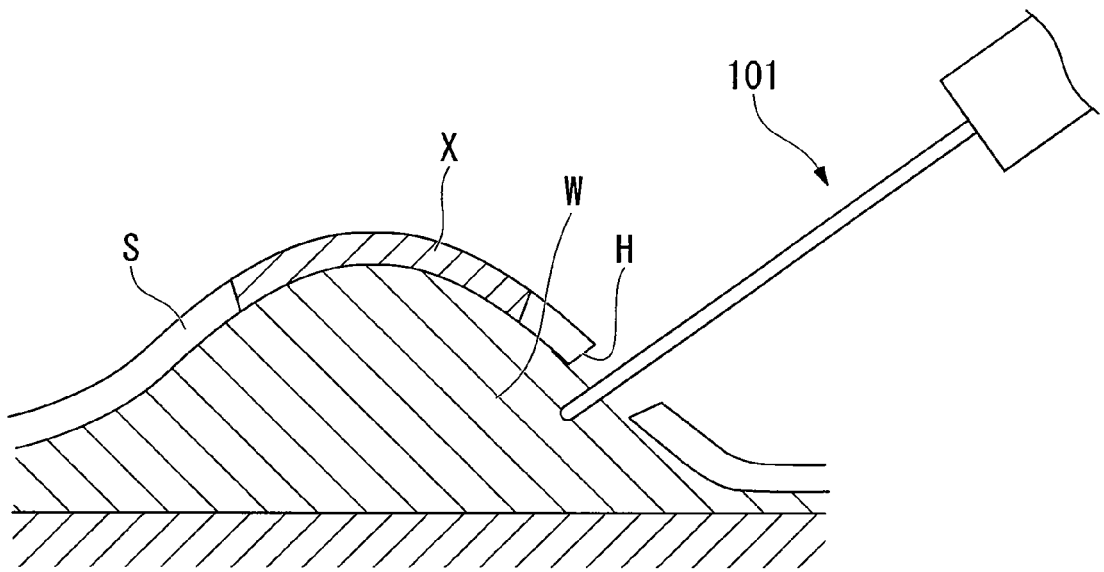
FIG. 7 illustrates a step of ESD.

Subsequently, the high-frequency knife 101 is inserted into the operation channel; the high-frequency knife 101 is made contact with a part of the mucosa S in the vicinity of the affected site X as shown in FIG. 7; and a hole H used for starting an encircling dissection is opened by applying high-frequency electric current. The submucosa W is then exposed by operating both the endoscope and the high-frequency knife 101 and dissecting the mucosa around the affected site X.

Figure 4:
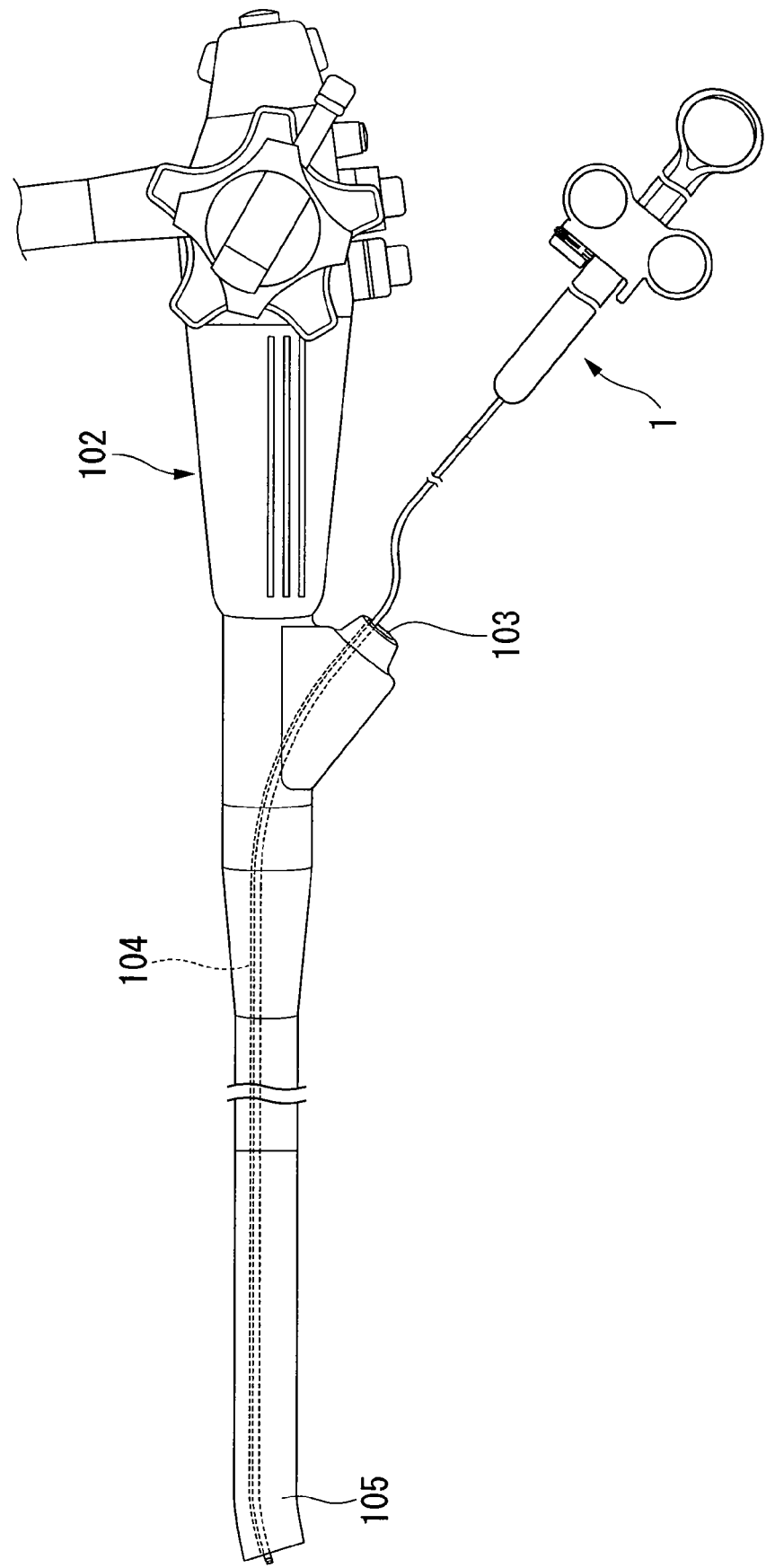
FIG. 4 shows the endoscopic-use treatment instrument inserted into the endoscope.

Subsequently, the high-frequency knife 101 is removed from the operation channel, and the treatment instrument 1 is inserted into the operation channel 104 as shown in FIG. 4.

More specifically, full proximal retraction (toward the ring 10B) of the slider 11 of the treatment instrument 1 causes the knife 2 to be enclosed into the sheath 4. The distal end of the sheath 4 is inserted from a forceps port 103 having an opening on the operation section of the endoscope 102 into the operation channel 104, and then, the distal end of the treatment instrument 1 is protruded from the distal end of the insertion section 105 of the endoscope 102. Subsequently, an electric power cord, not shown in the drawing, is connected to the plug 14. The electric power cord may be connected prior to insertion of the treatment instrument 1 into the endoscope 102.

Upon approaching the distal end of the treatment instrument 1 to the affected site X, the user extends the slider 11 and protrudes the knife 2 from the sheath 4. Subsequently, the operation section 5 is rotated to adjust the Y-letter shape of the knife 2 to be substantially horizontal with respect to the affected site X.

More specifically, the user holding the rotor 12 with one hand rotates the main body 10 and the slider 11 of the operation section 5. Rotational operation by the operation section 5 rotates the wire 3, and torque thereof is transferred to the knife 2.

The distal end of the knife 2 protruding ahead of the regulator member 9 is freely rotative relative to the regulator member 9 and the rotational member 8 until the expansion section 2A of the knife 2 engages with the groove 9B of the regulator member 9. The expansion section 2A engages with one of the grooves 9B while rotating at least 90 degrees. The rotation of the knife 2 relative to the rotational member 8 is regulated by engaging the expansion section 2A with the groove 9B since the regulator member 9 is fixed to the rotational member 8 unitarily. After that, the knife 2, the regulator member 9, and the rotational member 8 rotates unitarily relative to the sheath 4 and the bearing 7.

Figure 8:
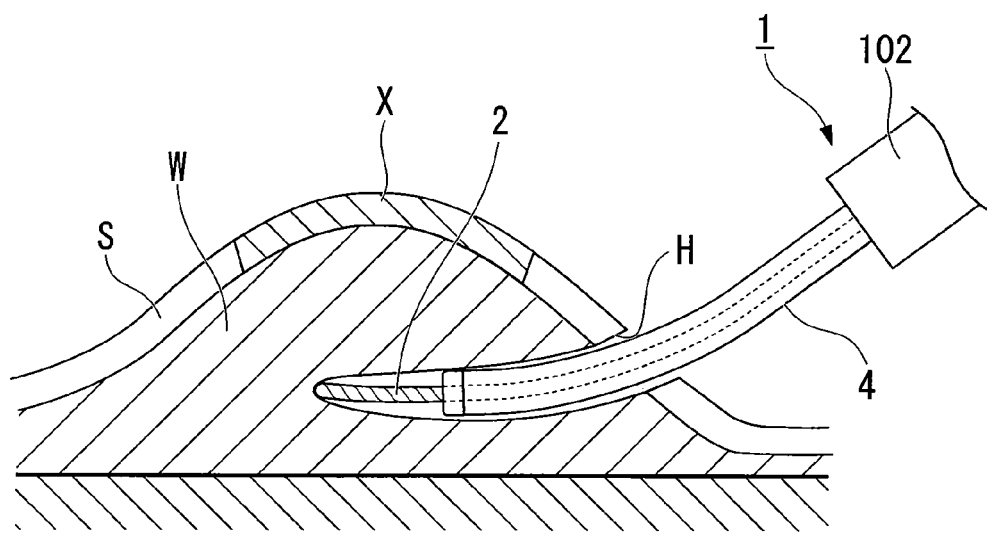
FIG. 8 illustrates a step of ESD.
Figure 9:
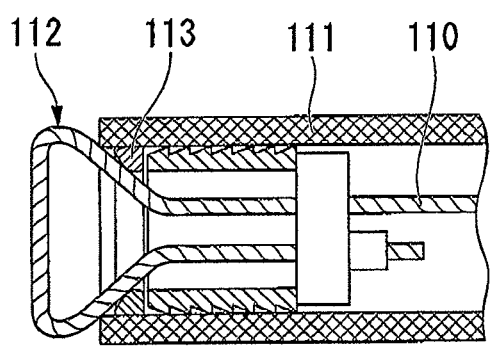
FIG. 9 shows the vicinity of distal end of a conventional endoscopic-use treatment instrument in fragmentary enlarged sectional view.

Subsequent to adjusting the correlation between the knife 2 and the affected site X, high-frequency electric current is applied to the submucosa W via the distal end of the knife 2 made contact with there while observing through the fixed state of endoscope 102, and then, the sheath 4 of the treatment instrument 1 is extended into the operation channel 104. Accordingly, as shown in FIG. 8, the submucosa W is dissected by the knife 2, and the affected site X is removed.

According to the treatment instrument 1 of the present embodiment, the rotation of the knife 2 relative to the rotational member 8 is regulated, and the knife 2, the regulator member 9, and the rotational member 8 rotate unitarily relative to the sheath 4 and the bearing 7 by engaging the expansion section 2A of the knife 2 with the groove 9B of the regulator member 9.

In this state, the knife 2 desirably rotates in correspondence with the rotational operation of the operation section since there will be hardly a friction between the bearing 7 and the rotational member 8 while the smoothly formed inner periphery 7B of the bearing 7 makes contact with the smoothly formed outer periphery 8C of the rotational member 8. Therefore, the treatment instrument can be configured which can rotate the knife 2 by a desirable rotational amount reliably by the rotational operation.

In addition, the knife 2 engages with one of the grooves 9B by rotating the wire 3 by at least 90 degrees since two pairs of grooves 9B are disposed on the regulator member 9 vertically and horizontally. Therefore, idle rotation, which prevents from controlling the distal end of the knife 2, can be reduced.

In addition, the knife 2 to which electric current is supplied can be insulated by the expansion section 2A reliably since the regulator member 9 is formed by an insulative material. Therefore, inadvertent damage to non-affected tissue can be prevented, and tissue-dissection can be operated desirably by concentrating electric energy to the distal end of the knife 2.

The technical scope of the present invention is not limited to the embodiment described above. Rather, various modifications may be added unless deviating from the spirit of the invention.

For example, the distal end mechanism is not limited to the aforementioned embodiment explained with reference to an example providing the Y-shaped knife 2 to the distal end of the treatment instrument. For example, a wire snare loop expanding in the exterior of a sheath or a grasping forceps having a pair of arm sections expanding upon protruding from a sheath can be applied to the treatment instrument of the present invention without problem since they are formed by flexible material and they expand in a radial direction of the sheath in the exterior of the sheath to fit or engage with a regulator member or a rotative member.

Also, the aforementioned distal end mechanism is not limited in using electric current. The regulator member may be formed by a conductive material, or the distal end mechanism free from the regulator member may be formed unitarily with the rotative member since insulation is unnecessary if electricity is not supplied to the distal end mechanism.

Furthermore, the shape of the regulator member is not limited to the aforementioned embodiment explained with reference to an example in which the grooves 9B of the regulator member serve as regulator members for regulating the rotation of the knife 2 relative to the rotational member 8. For example, the knife 2, the regulator member 9, and the rotational member 8 may be configured to rotate unitarily by fixing a ring member, e.g. rubber, having a significant friction coefficient into the inner periphery of the through-hole 9A of the regulator member 9 in the vicinity of the distal end thereof by crimping method, etc. and engaging the ring member with the expansion section 2A of the knife 2 by the friction force.

In addition, a regulator member may be configured to engage with the knife 2 by providing the structure of the grooves 9B to the inner periphery of the rotational member 8. In addition, similar shape may be formed to the distal end surface of the flange 8A of the rotational member 8, and a projecting section having the corresponding engageable shape may be formed to the stopper 6.

What is claimed is:

1. An endoscopic-use treatment instrument, comprising:
   a wire;
   a treatment member formed by a flexible material, the treatment member being disposed at a distal end of the wire and used for treatment conducted in a body cavity;
   a flexible sheath having the wire passing therethrough;
   an operation section provided to a proximal end of the wire and capable of rotating the wire around an axial line;
   a cylindrical bearing fixed to a distal end of the flexible sheath;
   a rotative member inserted into the cylindrical bearing and capable of freely rotating relative to the bearing; and
   a regulator section provided to the rotative member and regulating rotation of the treatment member relative to the rotative member around the axial line, wherein
   the treatment member is urged to expand outward in a radial direction of the flexible sheath when the treatment member is exterior to the flexible sheath, and the rotation of the treatment member relative to the rotative member around the axial line is regulated when the treatment member makes direct contact with the regulator section.

2. The endoscopic-use treatment instrument according to claim 1, wherein the regulator section is disposed at a plurality of positions in a circumferential direction of the rotative member.

3. The endoscopic-use treatment instrument according to claim 1, further comprising a current-carrying member, disposed to make contact with the wire, for supplying electric current to the wire, wherein the treatment member is a wire treatment electrode, and the regulator section is formed by insulative material.

4. The endoscopic-use treatment instrument according to claim 2, further comprising a current-carrying member, disposed to make contact with the wire, for supplying electric current to the wire, wherein the treatment member is a wire treatment electrode, and the regulator section is formed by insulative material.

* * * * *